US009402847B2

(12) United States Patent
Davies

(10) Patent No.: US 9,402,847 B2
(45) Date of Patent: Aug. 2, 2016

(54) COMBINATIONS COMPRISING (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

(75) Inventor: Barry Robert Davies, Cheshire (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 14/008,459

(22) PCT Filed: Apr. 2, 2012

(86) PCT No.: PCT/GB2012/050736
§ 371 (c)(1),
(2), (4) Date: Jan. 15, 2014

(87) PCT Pub. No.: WO2012/131399
PCT Pub. Date: Oct. 4, 2012

(65) Prior Publication Data
US 2014/0121227 A1 May 1, 2014

Related U.S. Application Data

(60) Provisional application No. 61/470,668, filed on Apr. 1, 2011.

(51) Int. Cl.
A61K 31/337 (2006.01)
A61K 31/519 (2006.01)
(52) U.S. Cl.
CPC ............. *A61K 31/519* (2013.01); *A61K 31/337* (2013.01)
(58) Field of Classification Search
CPC .......................... A61K 31/337; A61K 31/519
See application file for complete search history.

(56) References Cited

U.S. PATENT DOCUMENTS

| | | | |
|---|---|---|---|
| 5,439,686 | A | 8/1995 | Desai et al. |
| 6,162,804 | A | 12/2000 | Bilodeau et al. |
| 6,432,947 | B1 | 8/2002 | Arnaiz et al. |
| 6,749,868 | B1 | 6/2004 | Desai et al. |
| 2002/0094974 | A1 | 7/2002 | Castelhano et al. |
| 2003/0045536 | A1 | 3/2003 | Castelhano et al. |
| 2003/0073708 | A1 | 4/2003 | Castelhano et al. |
| 2003/0139427 | A1 | 7/2003 | Castelhano et al. |
| 2004/0014694 | A1 | 1/2004 | Chakroun |
| 2004/0082598 | A1 | 4/2004 | Castelhano et al. |
| 2004/0082599 | A1 | 4/2004 | Castelhano et al. |
| 2006/0111362 | A1 | 5/2006 | Kira et al. |
| 2006/0148844 | A1 | 7/2006 | Nakade et al. |
| 2007/0082838 | A1 | 4/2007 | De et al. |
| 2007/0117744 | A1 | 5/2007 | Desai et al. |
| 2007/0135402 | A1 | 6/2007 | Habashita et al. |
| 2008/0070936 | A1 | 3/2008 | Castelhano et al. |
| 2008/0108612 | A1 | 5/2008 | Carrez et al. |
| 2008/0119467 | A1 | 5/2008 | Carrez et al. |
| 2008/0131526 | A1* | 6/2008 | Sebti ................ A61K 39/39558 424/649 |
| 2008/0161382 | A1 | 7/2008 | Desai et al. |

FOREIGN PATENT DOCUMENTS

| | | |
|---|---|---|
| EP | 1444982 A1 | 8/2004 |
| GB | 1047935 A1 | 9/1966 |
| WO | WO 95/00516 A1 | 1/1995 |
| WO | WO 97/38665 A2 | 10/1997 |
| WO | WO 99/07703 A1 | 2/1999 |
| WO | WO 99/62908 A2 | 12/1999 |
| WO | WO 99/65909 A1 | 12/1999 |
| WO | WO 00/75145 A1 | 12/2000 |
| WO | WO 01/07050 A1 | 2/2001 |
| WO | WO 01/14371 A1 | 3/2001 |
| WO | WO 02/00661 A1 | 1/2002 |
| WO | WO 02/18348 A3 | 3/2002 |
| WO | WO 02/057267 A1 | 7/2002 |
| WO | WO 02/076484 A2 | 10/2002 |
| WO | WO 03/057696 A1 | 7/2003 |
| WO | WO 03/088908 A3 | 10/2003 |
| WO | 03097164 A1 | 11/2003 |
| WO | WO 2004/014850 A3 | 2/2004 |
| WO | WO 2004/021979 A2 | 3/2004 |
| WO | WO 2004/043380 A3 | 5/2004 |
| WO | WO 2004/080463 A1 | 9/2004 |
| WO | WO 2004/094426 A1 | 11/2004 |
| WO | WO 2005/003128 A1 | 1/2005 |
| WO | WO 2005/020921 A3 | 3/2005 |
| WO | WO 2005/026149 A1 | 3/2005 |
| WO | WO 2005/044181 A3 | 5/2005 |
| WO | WO 2005/051304 A3 | 6/2005 |
| WO | WO 2005/117909 A3 | 12/2005 |

(Continued)

OTHER PUBLICATIONS

Eniu et al. The Oncologist, 2005, vol. 10, pp. 665-685.*
Bales et al., 'Use of F-FDG PET as a biomarker to demonstrate activity of the novel AKT inhibitor AZD5363 in a xenograft model', AACR (Apr. 4, 2011); 1030.
Barnett et al., 'The Akt-PKB Family of Protein Kinases: A Review of Small Molecule Inhibitors and Progress Towards Target Validation', Current Topics in Medicinal Chemistry (2005); 5; 109-125.

(Continued)

Primary Examiner — James D Anderson
(74) Attorney, Agent, or Firm — Daniel Kopp

(57) ABSTRACT

The present invention relates to a combination comprising (S)-4-amino-N-(1-(4-chlorophenyl)-3-hydroxypropyl)-1-(7H-pyrrolo[2,3-d]pyrimidin-4-yl)piperidine-4-carboxamide, or a pharmaceutically acceptable salt thereof, hereafter "Compound (I)", and a taxane. Taxanes include established cancer drugs such as docetaxel (Taxotere™) and paclitaxel (Taxol™). Such combinations may be useful in the treatment or prophylaxis of cancer. The invention also relates to a pharmaceutical composition comprising such Compound (I) and a taxane. The invention further relates to a method of treatment comprising the simultaneous, sequential or separate administration of Compound (I) and a taxane, to warm-blooded animal, such as man. The invention also relates to a kit comprising Compound (I) and a taxane, optionally with instructions for use.

6 Claims, 3 Drawing Sheets

(56) References Cited

FOREIGN PATENT DOCUMENTS

Figure 1:
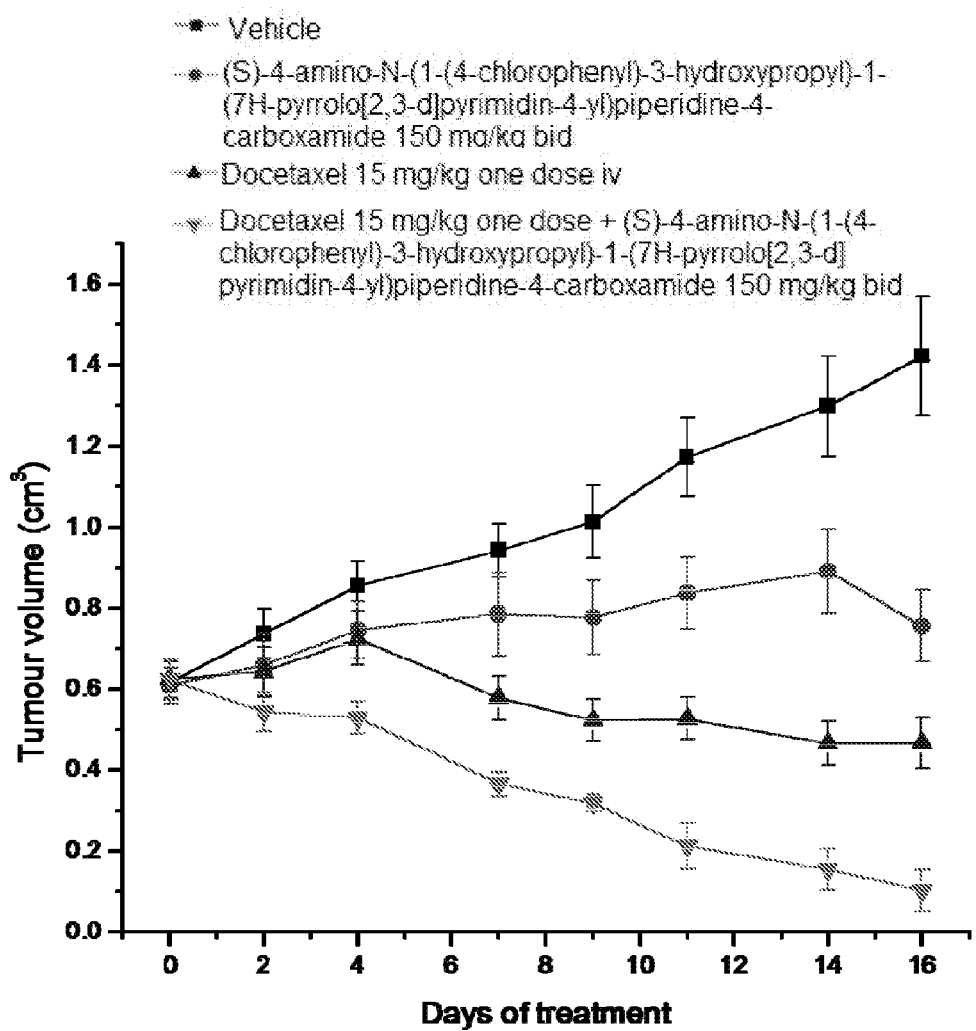

| WO | WO 2006/046023 A1 | 5/2006 |
|---|---|---|
| WO | WO 2006/046024 A1 | 5/2006 |
| WO | WO 2006/071819 A1 | 7/2006 |
| WO | WO 2006/075094 A3 | 7/2006 |
| WO | WO 2006/075095 A3 | 7/2006 |
| WO | WO 2006/091450 A1 | 8/2006 |
| WO | WO 2006/135639 A1 | 12/2006 |
| WO | WO 2007/007919 A2 | 1/2007 |
| WO | WO 2007/025090 A3 | 3/2007 |
| WO | WO 2007/084667 A3 | 7/2007 |
| WO | WO 2007/125310 A3 | 11/2007 |
| WO | WO 2007/125315 A3 | 11/2007 |
| WO | WO 2007/125320 A1 | 11/2007 |
| WO | WO 2007/125321 A3 | 11/2007 |
| WO | WO 2007/125325 A1 | 11/2007 |
| WO | WO 2008/075109 A1 | 6/2008 |
| WO | WO 2008/075110 A1 | 6/2008 |
| WO | WO 2008/079346 A1 | 7/2008 |
| WO | WO 2009/047563 A1 * | 4/2009 |

OTHER PUBLICATIONS

Bradley et al., 'Tumor targeting by covalent conjugation of a natural fatty acid to paclitaxel', Clin. Cancer Res. (2001); 7; 3229-38.

Davies et al., 'Characterization of AZD5363, an orally bioavailable, potent ATP-competitive inhibitor of AKT kinases with pharmacodynamic and antitumor activity in preclinical models', AACR (Apr. 4, 2011); 4477.

Greenwood et al., 'In vitro mechanism of action of AZD5363, a novel AKT inhibitor, in breast and prostate cancer cell lines', AACR (Apr. 4, 2011); 1052.

IPRP for corresponding PCT application. Application No. PCT/GB2008/050925; mailed Apr. 22, 2010.

Lamoureux et al., 'AZD5363 a novel Akt inhibitor delays prostate cancer progression by inhibiting androgen-receptor activity', The Vancouver Prostate Centre and AstraZeneca (Apr. 4, 2011).

Luke et al., 'Discovery of AZD5363 in orally bioavailable potent ATP-competitive inhibitor of AKT kinases', AACR (Apr. 4, 2011); 4478.

Mackay, 'Transforming Drug Discovery Innovative Platforms', Pfizer (Nov. 30, 2006).

Opposition filed against corresponding application in Dominican Republic, Patent Application No. P2010-0103; mailed Aug. 20, 2010.

Opposition filed against corresponding application in Ecuador, Patent Application No. SP-10-10093; mailed Oct. 13, 2010.

Opposition filed against corresponding application in Costa Rica, Patent Application No. 11.359; mailed Nov. 1, 2010.

Quintela et al.,'Pyrazolopyrimidines: synthesis, effect on histamine release from rat peritoneal mast cells and cytotoxic activity', Eur. J Med. Chem. (2001); 36; 321-332.

* cited by examiner

Change in tumour volume in HCC-1187 breast cancer model using various intermittent dosage schedules:

- ■ Vehicle

- ● Docetaxel 5 mg/kg once weekly

- ▲ AZD5363 - 300 mg/kg qd, 4 days on, 3 days off.

- ▼ AZD5363 - 300 mg/kg qd, 4 days on, 3 days off, plus docetaxel 5 mg/kg once weekly, (docetaxel dosed 1 hour before the AZD5363).

- ◄ AZD5363 - 300 mg/kg qd, 4 days on, 3 days off, plus docetaxel 5 mg/kg once weekly, (docetexel dosed 1 day after the AZD5363).

- ► AZD5363 - 300 mg/kg qd, 4 days on, 3 days off, plus docetaxel 5 mg/kg once weekly, (docetexel dosed 1 day before the first dose of AZD5363).

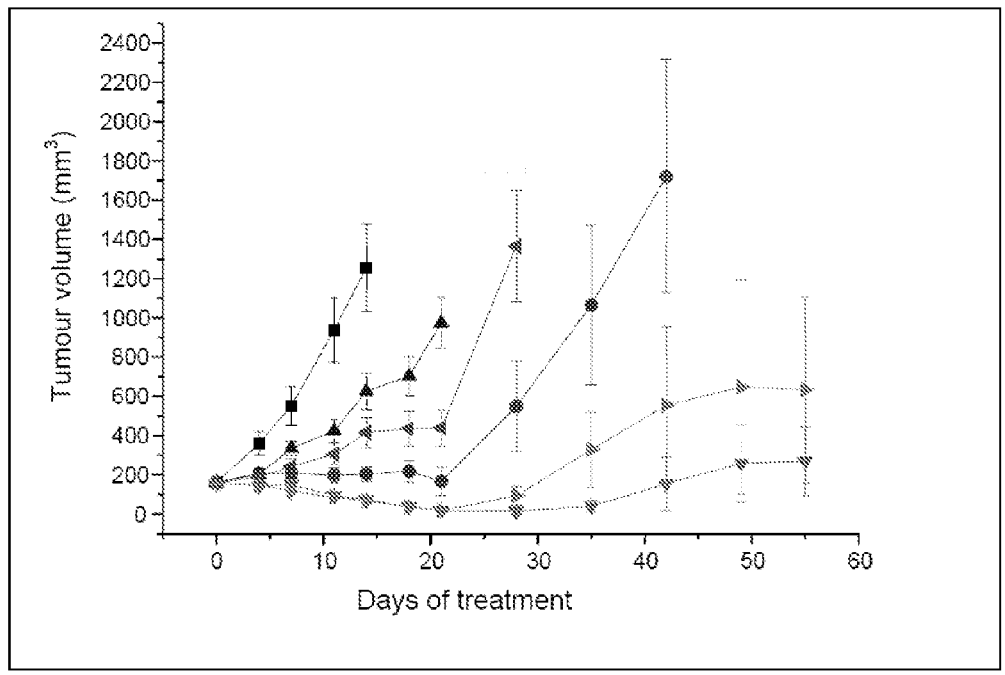

Figure 3

COMBINATIONS COMPRISING (S)-4-AMINO-N-(1-(4-CHLOROPHENYL)-3-HYDROXYPROPYL)-1-(7H-PYRROLO[2,3-D]PYRIMIDIN-4-YL)PIPERIDINE-4-CARBOXAMIDE

This application is a 35 U.S.C. §371 national stage entry of International Application No. PCT/GB2012/050736, filed Apr. 2, 2012, and claims priority under 35 U.S.C. §119(e) to U.S. provisional application Ser. No. 61/470,668, filed Apr. 1, 2011, entitled "Therapeutic Treatment", the contents of which are hereby incorporated by reference.

The present invention relates to a combination comprising (S)-4-amino-N-(1-(4-chlorophenyl)-3-hydroxypropyl)-1-(7H-pyrrolo[2,3-d]pyrimidin-4-yl)piperidine-4-carboxamide, or a pharmaceutically acceptable salt thereof, hereafter "Compound (I)", and a taxane. Taxanes include established cancer drugs such as docetaxel (Taxotere™) and paclitaxel (Taxol™). Other taxanes are cabazitaxel, larotaxel, ortataxel, tesetaxel. Such combinations may be useful in the treatment or prophylaxis of cancer. The invention also relates to a pharmaceutical composition comprising such Compound (I) and a taxane. The invention further relates to a method of treatment comprising the simultaneous, sequential or separate administration of Compound (I) and a taxane to warm-blooded animal, such as man. The invention also relates to a kit comprising Compound (I) and a taxane, optionally with instructions for use.

Cancer affects an estimated 10 million people worldwide. This figure includes incidence, prevalence and mortality. More than 4.4 million cancer cases are reported from Asia, including 2.5 million cases from Eastern Asia, which has the highest rate of incidence in the world. By comparison, Europe has 2.8 million cases, North America 1.4 million cases, and Africa 627,000 cases.

In the UK and US, for example, more than one in three people will develop cancer at some point in their life. Cancer mortality in the U.S. is estimated to account for about 600,000 a year, about one in every four deaths, second only to heart disease in percent of all deaths, and second to accidents as a cause of death of children 1-14 years of age. The estimated cancer incidence in the U.S. is now about 1,380,000 new cases annually, exclusive of about 900,000 cases of non-melanotic (basal and squamous cell) skin cancer.

Cancer is also a major cause of morbidity in the UK with nearly 260,000 new cases (excluding non-melanoma skin cancer) registered in 1997. Cancer is a disease that affects mainly older people, with 65% of cases occurring in those over 65. Since the average life expectancy in the UK has almost doubled since the mid nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer. In people under the age of 75, deaths from cancer outnumber deaths from diseases of the circulatory system, including ischaemic heart disease and stroke. In 2000, there were 151,200 deaths from cancer. Over one fifth (22 percent) of these were from lung cancer, and a quarter (26 percent) from cancers of the large bowel, breast and prostate.

Worldwide, the incidence and mortality rates of certain types of cancer (of stomach, breast, prostate, skin, and so on) have wide geographical differences which are attributed to racial, cultural, and especially environmental influences. There are over 200 different types of cancer but the four major types, lung, breast, prostate and colorectal, account for over half of all cases diagnosed in the UK and US.

Current options for treating cancers include surgical resection, external beam radiation therapy and/or systemic chemotherapy. These are partially successful in some forms of cancer, but are not successful in others. There is a clear need for new therapeutic treatments.

Compound (I) (in the free base form) is shown below:

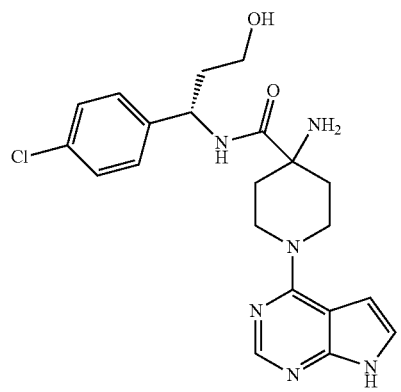 [SMILES: NC1(C(=O)N[C@@H](CCO)c2ccc(Cl)cc2)CCN(c2ncnc3[nH]ccc23)CC1]

Compound (I) (in free base form) is also known as AZD5363.

Compound (I) (in free base form) was disclosed in international patent application publication No. WO2009/047563. In WO2009/047563 it is stated that compounds disclosed therein may be applied as a sole therapy or may involve, in addition to a compound of the invention, conventional surgery, radiotherapy or chemotherapy. WO2009/047563 then lists many potential anti-tumour agents. Nowhere in WO2009/047563 is the specific combination of Compound (I) and a taxane disclosed.

Surprisingly, according to the present invention, it has been found that the combination use of Compound (I) with a taxane may have a particular benefit in the treatment of cancer. As illustrated hereinafter, the use of a combination comprising both Compound (I) and a taxane (docetaxel) provides more than an additive effect at regulating tumour volume, compared with the use of either component alone.

Therefore, according to the first aspect of the present invention there is provided a combination comprising Compound (I) and a taxane.

Herein where the term "taxane" is used it is to be understood that this may refer to any chemical analogue which exerts its anticancer effect by stabilization of the tubulin microtubules involved in cell division.

Examples of taxanes that may be combined with Compound (I) include: (2aR,3aR,4aR,6R,9S,11S,12S,12aR,12bS)-6,12b-diacetoxy-9-[3 (S)-(tert-butoxycarbonylamino)-2-(R)-hydroxy-3-phenylpropionyloxy]-12-benzoyloxy-11-hydroxy-8,13,13-trimethyl-2a,3,3a,4,5,6,9,10,11,12,12a,12b-dodecahydro-1H-7,11-methanocyclodeca[3,4]-cyclopropa[4,5]benz[1,2-b]oxet-5-one dihydrate; paclitaxel (Taxol), BMS-184476 (7-methylthiomethylpaclitaxel); BMS-188797; BMS-275183; BMS-188797; BMS-109881; CYC-3204 (a penetratin-paclitaxel conjugate); Taxoprexin; DJ-927; Docetaxel (Taxotere™); Larotexel (XRP9881; RPR-109881A); XRP6258 (RPR112658); Milataxel (MAC-321); MST 997; MBT-206; NBT-287; Ortataxel; Protax-3; PG-TXL; PNU-166945; PNU-106258; Orataxel (BAY 59-8862; IDN 5109; semisynthetic taxane); TPI-287; Protaxel and MAC-321 (Taxalog).

Examples of formulations for taxanes include conventional formulations of paclitaxel or docetaxel, for example the currently approved Taxol™ and Taxotere™ formulations;

formulations with biocompatible polymers, particularly proteins such as albumin, more particularly nano-particle or micro-particle formulations of paclitaxel or docetaxel with albumin, for example Abraxane™ (described in U.S. Pat. No. 5,439,686 and U.S. Pat. No. 6,749,868) or NAB-docetaxel (described in, for example US 20080161382, US20070117744 and US 20070082838);

polymer conjugates, particularly polymer conjugates of paclitaxel or docetaxel, more particularly conjugates of docetaxel or paclitaxel with poly-L-glutamate, for example Opaxio (also known as Xyotax, paclitaxel poliglumex, CT-2103 and described in for example Li C.; Poly (L-glutamic acid)—anticancer drug conjugates; Adv. Drug Deliv. Rev. 2002; 54: 695 713);

conjugates of docetaxel or paclitaxel with a fatty acid, particularly conjugates of paclitaxel or docetaxel with docosahexaenoic acid (DHA), for example, Taxoprexin (DHA-paclitaxel, described in for example Bradley M O et al. Tumor targeting by covalent conjugation of a natural fatty acid to paclitaxel; Clin. Cancer Res. 2001; 7: 3229-38);

microparticle compositions such as the porous microparticle formulations described in U.S. Pat. No. 6,645,528, for example the microparticle formulation of paclitaxel AI-850, comprising paclitaxel nanoparticles in a porous, hydrophilic matrix, composed primarily of a sugar; and emulsions of paclitaxel or docetaxel in vitamin E, for example Tocosol.

In one embodiment the taxane is selected from paclitaxel, docetaxel and Abraxane.

In a further embodiment the taxane is selected from docetaxel and paclitaxel.

In one embodiment the taxane is paclitaxel.

In another embodiment the taxane is docetaxel.

In a further embodiment the taxane is Abraxane.

In a further embodiment the taxane is cabazitaxel.

In one embodiment the taxane is selected from docetaxel, paclitaxel, cabazitaxel, larotaxel, ortataxel and tesetaxel.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the benefit of the effect arising from use of the combination. Therefore, in one embodiment sequential treatment involves administration of each component of the combination within a period of 11 days. In another embodiment this period is 10 days. In another embodiment this period is 9 days. In another embodiment this period is 8 days. In another embodiment this period is 7 days. In another embodiment this period is within 6 days. In another embodiment this period is within 5 days. In another embodiment this period is within 4 days. In another embodiment this period is within 3 days. In another embodiment this period is within 2 days. In another embodiment this period is within 24 hours. In another embodiment this period is within 12 hours.

As shown hereinafter, the Compound (I) can greatly sensitise to a single dose of docetaxel in the BT474c model, and an intermittent dosage schedule may have similar effectiveness at regulating tumour size as a continuous dosage schedule. It may be advantageous, within a given dosage cycle, to administer one specific component of the combination before the other—i.e. sequential dosing. Surprisingly, as described hereinafter, in the context of an intermittent dosage schedule, it has been found that there are significant differences in the degree of tumour growth delay achieved, depending upon the relative timing of dosing of Compound (I) vs the taxane.

Therefore, in one embodiment the sequential administration comprises the sequential administration of the Compound (I) prior to the administration of the taxane within a dosage cycle.

In another embodiment the sequential administration comprises the sequential administration of the taxane prior to the administration of Compound (I) (e.g. AZD5363) within a dosage cycle.

In one embodiment the sequential administration comprises the sequential administration of the taxane only within the 2 days prior to the first administration of Compound (I) (e.g. AZD5363) within a dosage cycle.

In one embodiment the sequential administration comprises the sequential administration of the taxane only within the 1 day prior to the first administration of Compound (I) (e.g. AZD5363) within a dosage cycle.

In one embodiment the sequential administration comprises the sequential administration of the taxane only within the 12 hours prior to the first administration of Compound (I) (e.g. AZD5363) within a dosage cycle.

In one embodiment the sequential administration comprises the sequential administration of the taxane only within the 6 hours prior to the first administration of Compound (I) (e.g. AZD5363) within a dosage cycle.

In one embodiment the sequential administration comprises the sequential administration of the taxane only within the 3 hours prior to the first administration of Compound (I) (e.g. AZD5363) within a dosage cycle.

In one embodiment the sequential administration comprises the sequential administration of the taxane only within the 1.5 hours prior to the first administration of Compound (I) (e.g. AZD5363) within a dosage cycle.

For the avoidance of doubt "within the x hours prior to the first administration of Compound" means any time up to x hours before the first dosing of Compound (I) (within a given dosage cycle) and includes substantially simultaneous dosing of the taxane with the first dosing of Compound (I) within a given dosage cycle.

In further embodiments the dosage cycle may be from 5 to 10 days in length.

In further embodiments the dosage cycle may be from 6 to 10 days in length.

In further embodiments the dosage cycle may be from 7 to 9 days in length.

In further embodiments the dosage cycle may be from 6 to 8 days in length.

In further embodiments the dosage cycle may be 10 days in length.

In further embodiments the dosage cycle may be 9 days in length.

In further embodiments the dosage cycle may be 8 days in length.

In further embodiments the dosage cycle may be 7 days in length.

In further embodiments the dosage cycle may be 6 days in length.

In further embodiments the dosage cycle may be 5 days in length.

In further embodiments the dosage cycle may involve Compound (I) (e.g. AZD5363) being dosed for 2-4 consecutive days and not being dosed for the other days within a dosage cycle of 6 to 9 days in length.

In further embodiments the dosage cycle may involve Compound (I) (e.g. AZD5363) being dosed for 3-4 consecutive days and not being dosed for the other days within a dosage cycle of 6 to 9 days in length; (for example, 7 days in length).

In further embodiments the dosage cycle may involve Compound (I) (e.g. AZD5363) being dosed for 3-5 consecutive days and not being dosed for the other days within a dosage cycle of 7 to 10 days in length.

In further embodiments the dosage cycle may involve Compound (I) (e.g. AZD5363) being dosed for 5 consecutive days and not being dosed for the other days within a dosage cycle of 6 to 9 days in length.

In further embodiments the dosage cycle may involve Compound (I) (e.g. AZD5363) being dosed for 4 consecutive days and not being dosed for the other days within a dosage cycle of 6 to 9 days in length; (for example, 7 days in length).

In further embodiments the dosage cycle may involve Compound (I) (e.g. AZD5363) being dosed for 3 consecutive days and not being dosed for the other days within a dosage cycle of 6 to 9 days in length.

In further embodiments the dosage cycle may involve the taxane being dosed on only one day during each dosage cycle.

Dosage cycles may be separated by a number of days where none of the active combination components are administered.

In one aspect where Compound (I) is mentioned, the Compound (I) is (S)-4-amino-N-(1-(4-chlorophenyl)-3-hydroxypropyl)-1-(7H-pyrrolo[2,3-d]pyrimidin-4-yl)piperidine-4-carboxamide; (i.e AZD5363).

In another aspect where Compound (I) is mentioned, the Compound (I) is a pharmaceutically acceptable salt of (S)-4-amino-N-(1-(4-chlorophenyl)-3-hydroxypropyl)-1-(7H-pyrrolo[2,3-d]pyrimidin-4-yl)piperidine-4-carboxamide.

A pharmaceutically acceptable salt of Compound (I) is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid.

In this specification any number of aspects or embodiments stated herein may be combined in any combination with each other (unless the context otherwise requires) to provide additional embodiments of the invention.

Where cancer is referred to, it may refer to oesophageal cancer, myeloma, hepatocellular cancer, pancreatic cancer, cervical cancer, ewings tumour, neuroblastoma, kaposis sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, brain cancer, renal cancer, lymphoma and leukaemia.

In one embodiment the cancer may be prostate cancer.

In one embodiment the cancer is castrate resistant prostate cancer.

In one embodiment the cancer is metastatic castrate resistant prostate cancer.

In one embodiment the cancer may be SCLC, NSCLC, colorectal cancer, ovarian cancer or breast cancer.

In one embodiment the cancer may be SCLC.

In one embodiment the cancer may be NSCLC.

In one embodiment the cancer may be colorectal cancer.

In one embodiment the cancer is gastric cancer.

In one embodiment the cancer may be ovarian cancer.

In one embodiment the cancer may be breast cancer.

In one embodiment the cancer is estrogen receptor positive breast cancer.

In one embodiment the cancer may be HER2-positive breast cancer.

In one embodiment the cancer may be bladder cancer, oesophageal cancer, gastric cancer, melanoma, cervical cancer or renal cancer.

In one embodiment the cancer may be endometrial, liver, stomach, thyroid, rectal or brain cancer.

In one embodiment the cancer may be is not melanoma.

In another embodiment the cancer is in a metastatic state, and more particularly the cancer produces metastases to the bone.

In a further embodiment of the invention, particularly the cancer is in a metastatic state, and more particularly the cancer produces skin metastases.

In a further embodiment of the invention, particularly the cancer is in a metastatic state, and more particularly the cancer produces lymphatic metastases.

In a further embodiment of the invention, the cancer is in a non-metastatic state.

(S)-4-Amino-N-(1-(4-chlorophenyl)-3-hydroxypropyl)-1-(7H-pyrrolo[2,3-d]-pyrimidin-4-yl)piperidine-4-carboxamide may be prepared according to the procedures described in WO2009/047563.

According to the present invention, there is provided a combination which comprises Compound (I) (e.g. AZD5363) and a taxane for use as a medicament.

According to a further aspect of the invention there is provided a pharmaceutical composition which comprises Compound (I) (e.g. AZD5363) and a taxane in association with a pharmaceutically acceptable diluent or carrier.

In one embodiment there is provided a pharmaceutical product comprising:
(i) a pharmaceutical composition which comprises Compound (I) (e.g. AZD5363) in association with a pharmaceutically acceptable diluent or carrier; and
(ii) a pharmaceutical composition which comprises a taxane in association with a pharmaceutically acceptable diluent or carrier.

In one aspect there is provided a method of treating cancer, in a warm-blooded animal, such as man, which comprises administering to said animal an effective amount of Compound (I) in combination with an effective amount of a taxane.

In one aspect where the treatment of cancer is indicated, it is to be understood that this may refer to the prevention of metastases and the treatment of metastases, i.e. cancer spread. Therefore the combination of the present invention might be used to treat a patient who has no metastases to stop them occurring, or to lengthen the time period before they occur, and to a patient who already has metastases to treat the metastases themselves. Furthermore the treatment of cancer may refer to treatment of an established primary tumour or tumours and developing primary tumour or tumours.

Therefore, in one aspect the treatment of cancer relates to the prevention of metastases.

In another aspect of the invention the treatment of cancer relates to the treatment of metastases.

In another aspect of the invention the treatment of cancer relates to treatment of an established primary tumour or tumours or developing primary tumour or tumours.

Herein, the treatment of cancer may refer to the prevention of cancer per se.

According to a further aspect of the invention, there is provided a kit comprising Compound (I) (e.g. AZD5363), and a taxane; optionally with instructions for use.

According to a further aspect of the invention, there is provided a kit comprising:
a) Compound (I) (e.g. AZD5363), in a first unit dosage form;
b) a taxane, in a second unit dosage form;
c) container means for containing said first and second dosage forms; and optionally
d) instructions for use.

An example of a unit dosage from for Compound (I) might be a tablet for oral administration.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 2 days prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 1 day prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 12 hours prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 6 hours prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 3 hours prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within the 1.5 hours prior to the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within 1.5 hours of the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within 3 hours of the first dosing of the Compound (I) within a given dosage cycle.

In one embodiment there is provided a kit comprising:
(i) a pharmaceutical composition which comprises Compound (I) (e.g. AZD5363) in association with a pharmaceutically acceptable dilent or carrier;
(ii) a pharmaceutical composition which comprises a taxane (e.g. docetaxel or paclitaxel) in association with a pharmaceutically acceptable diluent or carrier;
(iii) instructions recommending that taxane is only to be dosed within 6 hours of the first dosing of the Compound (I) within a given dosage cycle.

In further embodiments there is provided a kit (as defined herein) further comprising a container means for and Compound (I) composition (i) and the taxane composition (ii).

In further embodiments there is provided a kit (as defined herein) wherein the Compound (I) composition (i) and the taxane composition (ii) are contained within a container. In further embodiments the container may comprise a box. In further embodiments the container may comprise blister packaging. In further embodiments the container (or container means) has the instructions (iii) displayed on the container (or container means). In further embodiments the container (or container means) has the instructions (iii) contained within the container (or container means).

According to a further aspect of the invention there is provided a pharmaceutical composition which comprises Compound (I) (e.g. AZD5363) and a taxane in association with a pharmaceutically acceptable diluent or carrier for use in the treatment of cancer.

According to a further aspect of the invention there is provided a pharmaceutical composition which comprises Compound (I) (e.g. AZD5363), in association with a pharmaceutically acceptable diluent or carrier, in combination with a pharmaceutical composition which comprises a taxane in association with a pharmaceutically acceptable diluent or carrier for use in the treatment of cancer.

The pharmaceutical compositions may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients.

According to a further aspect of the present invention there is provided a kit comprising Compound (I) (e.g. AZD5363) and a taxane; optionally with instructions for use; for use in the treatment of cancer.

According to a further aspect of the present invention there is provided a kit comprising:
a) Compound (I) (e.g. AZD5363), in a first unit dosage form;
b) a taxane in a second unit dosage form; and
c) container means for containing said first and second dosage forms; and optionally
d) instructions for use;
for use in the treatment of cancer.

According to another feature of the invention there is provided the use of Compound (I) (e.g. AZD5363), in combination with a taxane in the manufacture of a medicament for the treatment of cancer.

In one embodiment there is provided the use of Compound (I) (e.g. AZD5363), in combination with a taxane in the manufacture of a medicament for the treatment of cancer wherein the taxane is only dosed within the 2 days prior to the first dosing of the Compound (I) within a given dosage cycle.

In one embodiment there is provided the use of Compound (I) (e.g. AZD5363), in combination with a taxane in the manufacture of a medicament for the treatment of cancer wherein the taxane is only dosed within the 1 day prior to the first dosing of the Compound (I) within a given dosage cycle.

In one embodiment there is provided the use of Compound (I) (e.g. AZD5363), in combination with a taxane in the manufacture of a medicament for the treatment of cancer wherein the taxane is only dosed within the 12 hours prior to the first dosing of the Compound (I) within a given dosage cycle.

In one embodiment there is provided the use of Compound (I) (e.g. AZD5363), in combination with a taxane in the manufacture of a medicament for the treatment of cancer wherein the taxane is only dosed within the 6 hours prior to the first dosing of the Compound (I) within a given dosage cycle.

In one embodiment there is provided the use of Compound (I) (e.g. AZD5363), in combination with a taxane in the manufacture of a medicament for the treatment of cancer wherein the taxane is only dosed within the 3 hours prior to the first dosing of the Compound (I) within a given dosage cycle.

In one embodiment there is provided the use of Compound (I) (e.g. AZD5363), in combination with a taxane in the manufacture of a medicament for the treatment of cancer wherein the taxane is only dosed within the 1.5 hours prior to the first dosing of the Compound (I) within a given dosage cycle.

Therefore there is provided the use of Compound (I) (e.g. AZD5363), in combination with a taxane in the manufacture of a medicament for the treatment of cancer, in a warm-blooded animal, such as man.

According to a further aspect of the present invention there is provided a combination comprising Compound (I) (e.g. AZD5363), and a taxane for use in the treatment of cancer.

In one embodiment there is provided a combination comprising Compound (I) (e.g. AZD5363) and a taxane for use in the treatment of cancer wherein the taxane is only dosed within the 2 days prior to the first dosing of the Compound (I) within a given dosage cycle.

In one embodiment there is provided a combination comprising Compound (I) (e.g. AZD5363) and a taxane for use in the treatment of cancer wherein the taxane is only dosed within the 1 day prior to the first dosing of the Compound (I) within a given dosage cycle.

In one embodiment there is provided a combination comprising Compound (I) (e.g. AZD5363) and a taxane for use in the treatment of cancer wherein the taxane is only dosed within the 12 hours prior to the first dosing of the Compound (I) within a given dosage cycle.

In one embodiment there is provided a combination comprising Compound (I) (e.g. AZD5363) and a taxane for use in the treatment of cancer wherein the taxane is only dosed within the 6 hours prior to the first dosing of the Compound (I) within a given dosage cycle.

In one embodiment there is provided a combination comprising Compound (I) (e.g. AZD5363) and a taxane for use in the treatment of cancer wherein the taxane is only dosed within the 3 hours prior to the first dosing of the Compound (I) within a given dosage cycle.

In one embodiment there is provided a combination comprising Compound (I) and a taxane for use in the treatment of cancer wherein the taxane is only dosed within the 1.5 hours prior to the first dosing of the Compound (I) within a given dosage cycle.

In one embodiment there is provided a combination comprising Compound (I) (e.g. AZD5363) and a taxane for use in the treatment of cancer wherein the taxane is only dosed within 1.5 hours of the first dosing of the Compound (I) within a given dosage cycle.

In one embodiment there is provided a combination comprising Compound (I) (e.g. AZD5363) and a taxane for use in the treatment of cancer wherein the taxane is only dosed within 3 hours of the first dosing of the Compound (I) within a given dosage cycle.

In one embodiment there is provided a combination comprising Compound (I) (e.g. AZD5363) and a taxane for use in the treatment of cancer wherein the taxane is only dosed within 6 hours of the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 2 days prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 1 day prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 12 hours prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 6 hours prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 3 hours prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within the 1.5 hours prior to the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within 1.5 hours of the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within 3 hours of the first dosing of the Compound (I) within a given dosage cycle.

According to a further aspect of the present invention there is provided a combination treatment comprising the administration of an effective amount of Compound (I) (e.g. AZD5363), optionally together with a pharmaceutically acceptable diluent or carrier, in combination with an effective amount of a taxane, optionally together with a pharmaceutically acceptable diluent or carrier, to a warm-blooded animal, such as man in need of such therapeutic treatment, for use in the treatment of cancer, wherein the taxane is only dosed within 6 hours of the first dosing of the Compound (I) within a given dosage cycle.

For the avoidance of doubt, "dosed within x hours of the first dosing" includes up to x hours before and up to x hours after the first dosing. The compositions of the invention may be obtained by conventional procedures using conventional pharmaceutical excipients, well known in the art. Thus, compositions intended for oral use may contain, for example, one or more colouring, sweetening, flavouring and/or preservative agents.

A compound such as Compound (I) may normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed, for example 4-7 mg/kg twice daily. However the daily dose will necessarily be varied depending upon the host treated, the particular route of administration, and the severity of the illness being treated. Accordingly the practitioner who is treating any particular patient may determine the optimum dosage. For example, a pharmaceutical composition of the present invention suitable for oral administration could comprise 1-200 mg/mL of Compound (I) in 0.5% hydroxypropylmethylcellulose (HPMC).

The taxane will normally be administered to a warm-blooded animal at a unit dose, of an amount known to the skilled practitioner as a therapeutically effective dose. For a single dosage form, the active ingredients may be compounded with an appropriate and convenient amount of excipients which may vary from about 5 to about 98 percent by weight of the total composition. Dosage unit forms will generally contain about 20 mg to about 500 mg of each active ingredient. However the daily dose will necessarily be varied depending upon the host treated, the particular route of administration, and the severity of the illness being treated. Accordingly the optimum dosage may be determined by the practitioner who is treating any particular patient.

In any embodiment described herein, the taxane (for example docetaxel or paclitaxel) may be dosed at 50-140 mg/m$^2$ of host/patient surface area on the day(s) when it is dosed, more preferably 60-120 mg/m$^2$, more preferably 65-110 mg/m$^2$. In any embodiment described herein, the AZD5363 content of Compound (I) may be dosed to a patient at 200-500 mg per day on days when it is dosed. The skilled person understands that if a pharmaceutically acceptable salt of AZD5363 is used, the AZD5363 content of Compound (I) is less than 100% and the actual mass of salt being dosed will be higher than the aforementioned 200-500 mg/day, depending on the mass of the counterion used to make the particular salt, and the stoichiometry of the salt. The actual doses to be used for a given patient should be determined by a appropriately qualified physician.

The dosage of each of the drugs and their proportions have to be composed so that the best possible treatment effects, as defined by national and international guidelines (which are periodically reviewed and re-defined), will be met.

LIST OF FIGURES

FIG. 1 shows the change in tumour volume in the BT474c model, over a 16-day period with (i) Compound (I) (as the free base) alone, (ii) a taxane alone (docetaxel), and (iii) the combination of the two together. Use of the combination appears to achieve significant tumour shrinkage.

Figure 2:
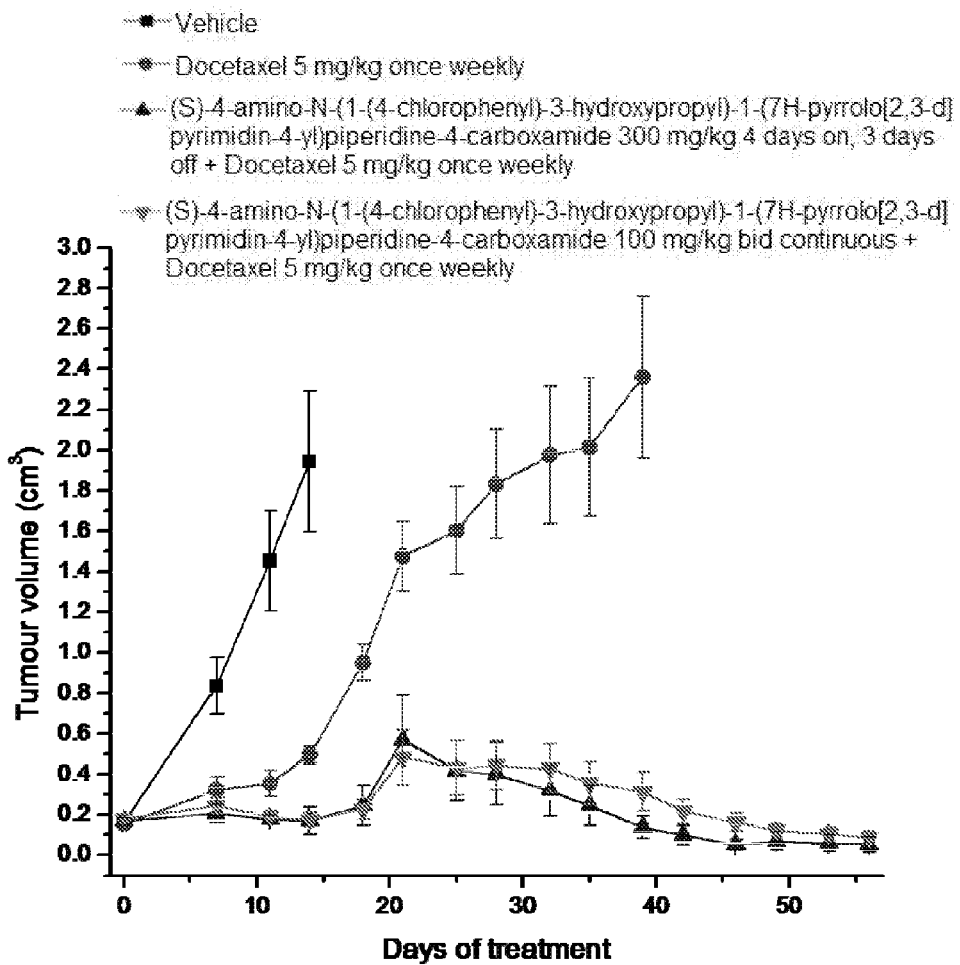

FIG. 2 shows the change in tumour volume in the HCC-1187 model, over a 55-day period with a taxane alone (docetaxel); and then intermittent and continuous schedules involving both Compound (I) (as the free base) with a taxane (decetaxel). This shows that two different dosage schedules (i.e. intermittent and continuous) can result in similarly sustained antitumour activity in combination with weekly cycles of docetaxel. In these experiments the indicated agent(s) where being administered in 2 weekly dosage cycles, then there was no dosing in the 3$^{rd}$ week (days 15-21 inclusive). The indicated agent(s) were again administered in further weekly dosage cycles from week 4 onwards.

FIG. 3 shows that the efficacy of combination between Compound (I) (in free base form, i.e. AZD5363) and a taxane (docetaxel), when AZD5363 is dosed intermittently, depends on the sequence of administration of the two agents: The data shows the effect of monotherapy and combinations of AZD5363 and docetaxel in HCC-1187 breast cancer xenografts. Animals were dosed with compounds over a 3 week period (3 weekly cycles of docetaxel and 3 weekly cycles of AZD5363 300 mg/kg once daily, 4 days on, 3 days off). The combination of AZD5363 and docetaxel resulted in greater efficacy than docetaxel monotherapy when docetaxel was dosed either 24 hours (day before) or 1 hour (same day) before the first administration of AZD5363, whereas if the docetaxel was administered 24 hours after the final dose of AZD5363, the effect was antagonistic i.e. the combination was less effective than docetaxel monotherapy. Following the 3 weekly cycles of treatment, animals were not treated with compound, and recovery of tumour growth was monitored. Of the different schedules that were investigated, it was found that administration of docetaxel 1 hour before AZD5363 resulted in the longest tumour growth delay.

EXPERIMENTAL DETAILS

Tumour cells were implanted subcutaneously into the flank of nude mice, then a tumour was allowed to grow in each mouse until it reached the desired starting volume for the particular experiment (approximately 0.6 cm$^3$ for the BT474c experiment, and approximately 0.15 cm$^3$ for the HCC-1187 experiment). The mice were then randomised into groups—each group destined to receive one of the four treatment regimes described in each of FIGS. 1 and 2. The mice were then dosed as described in FIGS. 1 and 2, where docetaxel was administered intravenously, and Compound (I) (as the free base) was administered orally. Calipers were used to monitor tumour sizes during these experiments, and the results are plotted on the graphs of FIGS. 1 and 2.

The BT-474 tumour cell line (human mammary carcinoma) was obtained from Dr Jose Baselga (at Laboratorio Recerca Oncologica, Paseo Vall D'Hebron 119-129, Barcelona 08035, Spain). This cell line was subcloned and a certain population referred herein to as BT474c was obtained. The HCC-1187 cell line is available from ATCC (www.atcc.org).

The invention claimed is:

1. A method for treating cancer, the method comprising administering to a human or animal in need of such treatment a therapeutically effective amount of (S)-4-amino-N-(1-(4-chlorophenyl)-3-hydroxypropyl)-1-(7H-pyrrolo[2,3-d]pyrimidin-4-yl)piperidine-4-carboxamide, in combination with a taxane,
    wherein the taxane is dosed prior to (S)-4-amino-N-(1-(4-chlorophenyl)-3-hydroxypropyl)-1-(7H-pyrrolo[2,3-d]pyrimidin-4-yl)piperidine-4-carboxamide, and wherein the taxane is only dosed within 1 day prior to a first dosing of the (S)-4-amino-N-(1-(4-chlorophenyl)-3-hydroxypropyl)-1-(7H-pyrrolo[2,3-d]pyrimidin-4-yl)piperidine-4-carboxamide within a given dosage cycle.

2. The method according to claim 1 wherein the taxane is selected from docetaxel and paclitaxel.

3. The method according to claim 1 wherein the cancer is breast cancer.

4. The method according to claim 1 wherein the dosage cycle comprises dosing (S)-4-amino-N-(1-(4-chlorophenyl)-3-hydroxypropyl)-1-(7H-pyrrolo[2,3-d]pyrimidin-4-yl)piperidine-4-carboxamide for 3-4 consecutive days and not dosing on other days within that same dosage cycle that is 6 to 9 days in length.

5. The method according to claim 1 wherein the taxane is dosed in an amount of 50-140 mg/m$^2$ of patient surface area on the day(s) dosed.

6. The method according to claim 1 wherein (S)-4-amino-N-(1-(4-chlorophenyl)-3-hydroxypropyl)-1-(7H-pyrrolo[2,3-d]pyrimidin-4-yl)piperidine-4-carboxamide is dosed to a patient wherein a content of (S)-4-amino-N-(1-(4-chlorophenyl)-3-hydroxypropyl)-1-(7H-pyrrolo[2,3-d]pyrimidin-4-yl)piperidine-4-carboxamide is administered in an amount of 200-500 mg per day on the days dosed.

* * * * *